(12) United States Patent
Hubbard et al.

(10) Patent No.: US 7,014,612 B2
(45) Date of Patent: Mar. 21, 2006

(54) METHOD FOR DIAGNOSIS OF HELICOBACTER PYLORI INFECTION

(75) Inventors: Todd W. Hubbard, Lake Forrest Park, WA (US); David L. Putnam, Sammamish, WA (US)

(73) Assignee: Photonic Biosystems, Inc., Sammamish, WA (US)

( * ) Notice: Subject to any disclaimer, the term of this patent is extended or adjusted under 35 U.S.C. 154(b) by 117 days.

(21) Appl. No.: 10/294,352

(22) Filed: Nov. 13, 2002

(65) Prior Publication Data

US 2004/0077965 A1 Apr. 22, 2004

Related U.S. Application Data

(60) Provisional application No. 60/331,275, filed on Nov. 13, 2001.

(51) Int. Cl.
*A61B 5/08* (2006.01)
*G01N 1/22* (2006.01)

(52) U.S. Cl. .................................. 600/532; 73/23.3
(58) Field of Classification Search ............... 600/529, 600/531, 532, 300; 73/23.3
See application file for complete search history.

(56) References Cited

U.S. PATENT DOCUMENTS

| | | | |
|---|---|---|---|
| 4,830,010 A | 5/1989 | Marshall | |
| 4,947,861 A | 8/1990 | Hamilton | |
| 5,543,621 A | 8/1996 | Sauke et al. | |
| 5,848,975 A | 12/1998 | Phillips | |
| 6,067,989 A | 5/2000 | Katzman | |
| 6,186,958 B1 | 2/2001 | Katzman et al. | 600/532 |
| 6,479,019 B1 | 11/2002 | Goldstein et al. | 422/84 |
| 6,491,643 B1 * | 12/2002 | Katzman et al. | 600/532 |
| 6,509,169 B1 * | 1/2003 | Ratcliffe et al. | 435/34 |

FOREIGN PATENT DOCUMENTS

| | | |
|---|---|---|
| DE | 29902593 U1 * | 7/1999 |
| WO | WO 97/26827 | 7/1997 |
| WO | WO 9730351 A1 * | 8/1997 |

OTHER PUBLICATIONS

NIH: Consensus Development Panel on Helicobacter pylori in Peptic Ulcer Disease. JAMA 272:65-69, 1994.
Graham: Camphylobacter detected non-invasively by $^{13}$C-Urea Breath Test. Lancet, May 23, 1987, p1174-1177.
Veldhuyzen van Zanten Sjo, Tytgat Maj, et al. $^{14}$C-Urea Breath Test for the Detection of Helicobacter pylori. Am. J. Gast. 85(4):399-403 (1990).
Marshall BJ, Plankey MW, et al. A 20-Minute Breath for Helicobacter pylori. Am. J. Gast. 86(4):438-445 (1991).
PYtest™, Tri-Med Specialties Inc. (division of Ballard Medical), Draper, UT 84020.

(Continued)

*Primary Examiner*—Max F. Hindenburg
*Assistant Examiner*—Navin Natnithithadha
(74) *Attorney, Agent, or Firm*—Barry L. Davison, J.D.; Davis Wright Tremaine LLP

(57) ABSTRACT

A rapid, non-invasive breath-test method and device for diagnosing the presence or absence of *H. pylori* in a subject without administration of isotopic tracers is described. The device consists of a highly sensitive colorimetric ammonia sensor placed in contact with sampled subject breath. The sensor is measured using appropriate reflection spectroscopy instrumentation. The breath-test method consists of measuring a basal ammonia level with the device, administering non-isotopic urea and continuing measurement of the ammonia content in a plurality of consecutive breaths. Diagnostic differences in breath ammonia are identified between *H. pylori* infected and uninfected individuals.

19 Claims, 11 Drawing Sheets

OTHER PUBLICATIONS

Mokuolu AO, Sigal, SH, Lieber CS. Gastric Juice Urease Activity as a Diagnostic Test for *Helicobacter pylori* Infection. Am. J. Gast. 92(4):644-648 (1997).

Thijs JC, van Zwet AA, et al. Diagnostic Tests for *Helicobacter pylori:* A Prospective Evaluation of Their Accuracy, without Selecting a Single Test as the Gold Standard.

Ito S, Miyaji H., et al. Hyperammonaemia and *Helicobacter pylori*. Lancet 346:124-5 Jul. 8, 1995.

Lipsky PS, Thomas JE, et al. Blood ammonia and *Helicobacter pylori*. Aust NZ J Med 22:311 (1992).

Plevris JN., Morgenstern R., et al. Hyperammonaemia in cirrhosis and *Helicobacter pylori* infection. Lancet:1104.

Jicong W, Guolong L., et al. $^{15}NH_4^+$ Excretion Test: a New Method for Detection of *Helicobacter pylori* Infection. J. Clin Micro. 30(1):181-4 (1992).

* cited by examiner

METHOD FOR DIAGNOSIS OF HELICOBACTER PYLORI INFECTION

RELATED APPLICATIONS

This application claims the benefit of the filing of U.S. Ser. No. 60/331,275 entitled "Method for Diagnosis of Helicobacter Pylori Infection" filed on Nov. 13, 2001, hereby incorporated by reference.

BACKGROUND

The present invention is directed to an effective diagnostic testing for the presence of gastric infection by the microorganism Helicobacter pylori.

Helicobacter pylori is estimated to be responsible for up to 90% of the cases of peptic ulcer disease (PUD) afflicts over 10% of the US population sometime in their lifetime. Estimates for worldwide prevalence of H. pylori infections range from 300 million to over two-thirds of the world's population. H. pylori infection is also associated with 650,000 annual cancer deaths worldwide from gastric adenocarcinoma. The US Communicable Disease Center recommends testing all patients presenting with PUD for diagnosis of H. pylori.

At present there are no test methods for H. pylori that satisfy the ideal conditions of being non-invasive, rapid, easy to administer, have low capital equipment and per-patient test costs, and capable of being conducted in entirety during a clinician's office visit. Currently practiced approaches for H. pylori testing can be broken down into invasive (endoscopy required) and non-invasive procedures. Examples of non-invasive tests include: determination of antibodies to H. pylori in blood, serum, or saliva; detection of H. pylori antigens in stool samples; and functional tests for the presence of the bacterium's urease enzyme with isotope-labeled urea breath tests (UBT).

Although the non-invasive antibody-based tests are relatively easy to perform, they have not proved to be reliable in the general practitioner's office. Furthermore, they incur a blood draw and the costs associated with the blood draw procedure. Additionally, antibody tests cannot provide a test-of-cure to demonstrate successful antibiotic treatment.

A variety of diagnostic procedures have evolved based on functional tests establishing presence of the urease enzyme produced by H. pylori. Urease, an enzyme found at high concentrations in the duodenum of infected individuals, hydrolyzes urea to ammonia ($NH_3$) and carbon dioxide ($CO_2$). Tests for gastric urease, vide infra H. pylori, rely on measures of the hydrolytic by-products of urea. With respect to non-invasive diagnosis, breath-based tests for expired isotopically-labeled $CO_2$ liberated from ingested isotopic urea are well known in the literature. Graham described a breath test for Camphylobacter (Helicobacter) based on measurement of $^{13}CO_2$ released after hydrolysis of ingested $^{13}C$-labeled urea (Graham, Lancet, May 23, 1987, p1174–1177). Others have used the rapid production of isotopically labeled $CO_2$ from ingested $^{14}C$-urea or $^{13}C$-urea to determine the presence or absence of the organism.

Measurement of ammonia production by the hydrolytic activity of urease is the basis for the invasive CLO and rapid urease tests. However, to execute these tests, invasive endoscopy procedures are required. They are therefore neither simple, economical, convenient for the patient, or executable in general clinical practices.

For a number of reasons, it has proven difficult to make measurements of breath ammonia liberated as a by-product of H. pylori urease. First, ammonia exists primarily as the ammonium ion at the physiologic pH of blood, and at the pH of gastric juice there is essentially no free ammonia. While ammonia readily crosses the stomach and alveolar lining, ammonium ions are not readily absorbed. Therefore very little ammonia finds its way from the stomach, traffics through the circulatory system, and passes into expired air, consequently making it difficult to measure.

A second major reason is the tight regulation of ammonia and ammonium levels by the liver and kidneys. Prior to general circulation, blood from the gut is circulated through the hepatic portal vein to the liver. Normally, the combination of periportal urea cycle enzymes and perivenous glutamine synthetase results in almost complete removal of $NH_3$ from blood flowing through the portal vein. Furthermore, at typical blood pH levels of 7.4, ammonia that does pass into the general circulation will exist primarily as ammonium ions that are removed by the kidney. This homeostatic regulatory system is therefore expected to minimize any fluctuations in circulating ammonia. Consequently, only minimal variations in breath ammonia would be expected either in normal individuals or, by comparison, individuals infected with H. pylori.

The literature corroborates the difficulty measuring ammonia directly in breath and lack of clinical evidence differentiating H. pylori individuals based on breath measures, such that a simple diagnosis via breath analysis is not expected. Lipski (Lipsky PS et al., Aust NZ J Med 22:311, 1992) and Plevris (Plevris JN et.al., Lancet:1104) found no difference in blood ammonia concentration between H. pylori positive and negative patients. Only by looking at $^{15}NH_4^+$ excretion in urine was Jicong (Jicong W et al., J. Clin Micro. 30(1):181–4, 1992) able to demonstrate a difference between pylori positive and negative subjects using nitrogen based assays. U.S. Pat. No. 4,947,861 suggests that by absorbing the water vapor from the breath prior to collecting a test sample, breath ammonia might be measured. However, he offers no evidence to demonstrate the utility of this maneuver and further, offers no teaching of its clinical utility or basis for deriving diagnoses. Similarly, Katzman (U.S. Pat. No. 6,067,989) suggests the use of near infrared analyzer for measuring breath changes in by-products ($CO_2$ & $NH_3$) of hydrolyzed isotopically labeled urea. Again however, Katzman's method does not teach diagnosis via ammonia, offering support only for measuring the $^{13}C$-labeled $CO_2$ by-product as measured by others (Graham DY et.al., Lancet, 1174–77, May 23, 1987).

Isotopic labeling has been critical in other breath measurement diagnostics for several reasons. Labeling provides advantage towards sensitive and specific distinction of the labeled reporter by-product using sophisticated instrumentation. The specific measurement of the label enables these assays to distinguish and quantify the urea hydrolysis product(s) in the presence of unlabled native hydrolysis products. For instance, as in the case of isotopic $CO_2$ based H. pylori breath testing, the use of $^{14}C$-labeled urea allows specific detection of the $^{14}CO_2$ urea byproduct at nanomolar concentrations despite millimolar $CO_2$ concentrations in the basal breath.

With respect to use of labeled urea, it is important to appreciate that the hydrolytic by-products of $CO_2$ and $NH_3$ generated within the gastrointestinal tract have vastly different fates within the body. As indicated, ammonia is tightly controlled by homeostatic mechanisms regulating physiological processing and circulating levels with little or no role for clearance by exhalation. In contrast, $CO_2$ has markedly different regulatory processes affecting its circulatory concentration with its major route for clearance occurring through the lungs. Therefore, despite labeled $CO_2$ being measurable in breath and serving diagnostically via the UBT method, it is not to be expected that ammonia would provide a parallel alternative avenue to diagnosis, much less be manifest in any diagnostically useful pattern in the breath.

There is a need for a simple, rapid non-invasive diagnostic test for *H. pylori*, based on measuring ammonia in breath, without the use of isotopically labeled reagent.

These and other limitations and problems of the past are solved by the present invention.

BRIEF SUMMARY OF THE INVENTION

A breath test device and method for determining the presence of *H. pylori* infection is disclosed and described including:

a) utilizing a sensing device capable of measuring ammonia at concentrations of between 50 ppb to 5000 ppb and a means for collecting and passing a breath sample to the sensor means;

b) measuring the basal ammonia in an individual's breath over a period of 0.5 to 5 minutes in a continuous or semi-continuous manner;

c) comparing the individual's basal breath ammonia against normative population values wherein *H. pylori* uninfected individuals display breath ammonia values above a predefined threshold and *H. pylori* infected individuals display breath ammonia values below said threshold;

d) administering a safe quantity of unlabeled urea to the subject and analyzing the subject's breath for the appearance of excess ammonia above the basal level; and e) comparing the individual's percentage change in post-urea breath ammonia against normal population values wherein *H. pylori* uninfected individuals display percentage changes below a predefined threshold and *H. pylori* infected individuals display percentage changes above a given threshold.

Alternatively, the follow-on urea administration and percentage change from basal measures can be utilized particularly on those individuals exhibiting intermediate basal results that are not definitive for the subject's *H. pylori* status as a means to more accurately identify infected individuals.

The method and device described herein satisfies therefore an unmet need for a simple, rapid non-invasive diagnostic test for *H. pylori*, based on measuring ammonia in breath, without the use of isotopically labeled reagent. Using highly sensitive calorimetric ammonia sensor membranes, a color analysis instrument to determine changes in the membrane's color and unlabeled urea, a subject's breath ammonia is analyzed prior to and after ingesting the urea. A remarkable and unexpected pattern in the breath ammonia measures has been discovered which is useful as a diagnostic. In addition to the instrument, sensor and materials, analytical methods for determining the *H. pylori* status of an individual without the use of isotopically labeled compounds is disclosed and described.

The invention will best be understood by reference to the following detailed description of the preferred embodiment, taken in conjunction with the accompanying drawings. The discussion below is descriptive, illustrative and exemplary and is not to be taken as limiting the scope defined by any appended claims.

DETAILED DESCRIPTION OF THE INVENTION

Figure 1A:
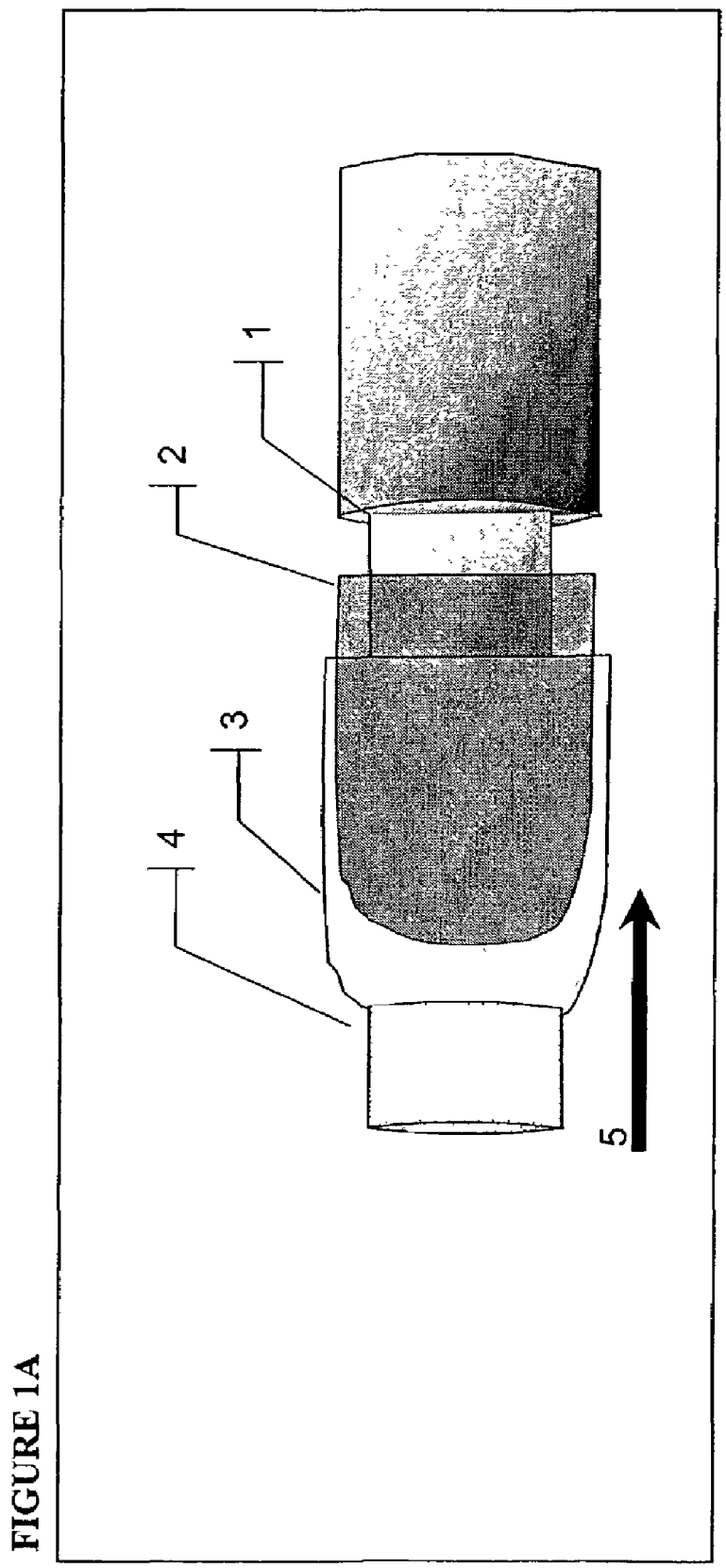
FIG. 1A is a dissolve view of the components of the optical sensor including a fiber optic 1 and FC type connector housing, a dyed sensor film 2, a undyed membrane overcoat 3 for protection and reflectance backing, a mechanical fit collar 4; and parts 5 slid over bullnose of FC connector to provide a tight fitting sheath.

A device for sensing ammonia in the breath and a method for conducting and interpreting diagnostic measures indicating the *Helicobacter pylori* clinical status of the subject is disclosed and described. Specifically, the device determines the *H. pylori* status of an individual by measurement of their breath ammonia both before and after oral administration of urea. Abnormally low basal breath ammonia measures (before urea administration) are diagnostic for the presence of *H. pylori*. After urea administration, increases in breath ammonia are indicative of *H. pylori* infection. Comparison of the relative change in breath ammonia before and after urea administration is even more predictive and is preferred for determining the presence or absence of *H. pylori*. Preferably, the comparison of the basal ammonia measure and the relative change in breath ammonia after urea administration are used together to predict the *H. pylori* infection status of the individual.

In one embodiment, the ammonia-sensing device utilizes an optical sensor that measures changes in ammonia concentration. In one aspect, the optical sensor includes a non-water soluble pH indicator dye, incorporated into an ammonia permeable solid-phase film or films (sensor films). Suitable dyes are chosen from a number of weak acid compounds that undergo sharp changes in their absorption spectra upon acid/base dissociation and include, but are not limited to, bromocresol green or bromophenol purple. The sensor films are composed of gas permeable hydrophobic polymers. In one aspect, these films may be porous. The polymers include Teflon® and related substituted ethylenic polymers.

Optical dyes are incorporated into sensor film by absorption methods using suitable solvents. Useful solvents are capable of dissolving the optical indicator dye and of wetting the hydrophobic sensor film. Such solvents include alcohols such as methanol, ethanol, and isopropanol as well as organic solvents such as THF and dichloromethane. Many other suitable solvents are known to those practiced in organic chemistry. In one aspect, deposition of the dye into the film is accomplished by dipping the film into the indicator dye solution followed by extensive rinsing of the membrane in water. Alternatively, the dye can be applied by spraying the solvent mixture onto the film followed by rinsing. An additional alternative would be to incorporate the dye directly into the film during its manufacture.

Residual dye is immobilized within the pores of the film such that gaseous ammonia permeates through the film, acting as a base with the indicator dye therein producing a change in the dye's spectral characteristic. The hydrophobic nature of the film prevents water and dissolved ions, including hydroxyl and hydronium ions, from interacting with the incorporated dye thereby making the optical sensor sensitive predominately to gaseous bases such as ammonia.

Ammonia induced color-change responses in the sensor film are preferably measured using optical absorption-based spectroscopy instruments. These instruments utilize reflectance measures of the pH dye's main absorption band. These reflection measures utilize two or more wavelengths including the main optical absorption band of the dye and a reference wavelength with changes unrelated to the dissociation state of the indicator dye. Illumination wavelengths can be provided by any suitable means known to those practiced in the art of optical instrumentation including tungsten-halogen, xenon, or light emitting diode lamps, among others. Detection of reflected light can be measured using photomultiplier tubes, PIN or other photosensitive devices and quantified using V/F, A/D or other methods well known to optical sensor practitioners.

Sensor films can be affixed to an optical window that allows for optical interrogation of the membrane by visual or instrument means. In one aspect, the optical window is the face of a waveguide. In another aspect, the waveguide is a fiber optic that allows insertion of the sensor film into the test environment with remote placement of the detection instrumentation. The ammonia breath-test (ABT) is most conveniently conducted by placing the optical ammonia sensor into the proximal port of a breathing tube, as close as possible to the subject's mouth as feasible. By placing the sensor close to the subject's mouth, the test minimizes adsorption of breath ammonia by breath condensate, plastic materials in the breath tube or other materials that act as an ammonia sink. Alternatively, the optical ammonia sensor may be placed close to the subject's nose in a nasal mask.

The ABT is conducted by measuring a fasted subject's breath before and after administering urea. In one embodiment of the method, the subject's normal exhalation is measured continuously for a period of up to 5 minutes to establish the individual's endogenous baseline, "basal measure", or "basal ammonia measure", of normally expired ammonia. Following determination of the basal ammonia measure, the subject is given a safe amount of urea to ingest. After ingestion of the urea, the subject's breath is measured after a period suitable to allow dissolution of the urea in the gastric contents and to be acted upon by any putative urease enzyme from the *H. pylori* organism to establish a post-urea ammonia measure or "post-urea measure".

Concurrent or subsequent to ingestion of the urea, the subject can be given materials or asked to perform physical maneuvers designed to enhance the urea hydrolysis to ammonia, ammonia release and/or its appearance in breath. As an example, a pH modifier such as $Al(OH)_3$ or $Mg(OH)_2$ can be administered to raise the stomach pH, shifting the equilibrium between ammonium and ammonia towards the latter. Other maneuvers designed to increase breath ammonia concentrations might include holding one's breath prior to exhalation or hyperventillating to change blood acid/base chemistry.

Non-isotopically labeled urea can be orally administered in a number of forms including capsules, liquids, sachets, or tablets. In one aspect, the urea is given such that only urease in the stomach can act on the administered urea. In another aspect, the urea is administered in a fast dissolving gelatin capsule (for example, less than 3 minutes to complete dissolution) with sufficient water to dissolve the capsule in the stomach. Twenty minutes was found adequate for dissolution, hydrolyis and subsequent appearance of ammonia on the subject's breath. This time might be minimized by delivering the urea in alternate forms such as liquid, liquid gel caps or other means of presolubilizing the urea.

The novel diagnostic method includes using the basal ammonia measure as a discriminator of infected versus uninfected individuals. The surprising results show *H. pylori* infected individuals have lower basal ammonia measures than uninfected individuals. Consequently, in one embodiment, the method for determining *H. pylori* status compares the basal ammonia ABT values against normative population standards.

It was also determined that after administering urea, the ammonia breath test values changed to a greater degree in infected than in non-infected individuals. As one example, 300 mg of urea was administered resulting in post-urea ammonia levels of 400 ppb to 1000 ppb ammonia. For this urea dose, the final post-urea ammonia ABT values are not diagnostic for the *H. pylori* status. Consequently, the method for determining *H. pylori* status compares the absolute or relative change between the basal ammonia measure and post-urea ammonia measure for an individual against normative general "population standards". The diagnostic test would utilize a combination of the basal ammonia measure and post-urea administration change ("post-urea ammonia measure") in breath ammonia measures to determine the *H. pylori* status of the individual.

EXAMPLES

The following examples are provided to illustrate the device used to measure breath ammonia, the method used to collect diagnostic breath ammonia measurements and the analytical methods for diagnosing *H. pylori* infection using the Ammonia Breath Test (ABT).

Example 1

Preparation of Ammonia Sensors for ABT and Optical Sensor Instrumentation

The following examples describe the preparation of an ammonia sensitive optical sensor useful for the direct determination of breath ammonia measures.

In one embodiment, the ABT sensor composition is made from an ammonia sensitive indicator dye and a solid phase, for example, a PTFE solid phase in a film form. In one aspect, the sensor compositions are constructed by administering ammonia-sensitive indicator dye(s) in a non-aqueous solvent to a solid-phase PTFE substrate such that the dye is deposited on the solid phase in a form insoluble to aqueous-based solvents. Further, the characteristics of a PTFE film or a porous membrane form are such that it is permeable to gaseous ammonia.

Optical sensor films for ABT were prepared by dissolving the optical dyes bromocresol-green (BCG) or bromophenol-blue (BPB) in methanol at a concentration of 0.75 mg/L. Other dyes, such as but not limited to, any fluorescent dyes such as H2TFPP or other pH sensitive dyes can be used. In this example, porous 1 $\mu$m PTFE films were dipped into the optical dye solutions for 20 seconds, although films of other thicknesses are envisioned. Alternatively, dye concentrations of about 0.25 mg/L to about 5 mg/L have been used to successfully prepare ammonia sensors with the required ammonia sensitivity for use in ABT measurements. After the film has been thoroughly wetted with the dye solution, the film is removed from the solution, blotted dry then washed extensively with deionized water. The washed sensor films were dried and stored in the dark.

Optical sensors 1 were prepared by placing a small piece of the bromocresol-green or bromophenol-blue dyed optical sensor film over the end of a 250 $\mu$m fiber optic potted in an FC-optical connector housing. The sensor films were then mechanically fixed in place by putting on an overlay of a second piece of undyed PTFE film around which a tight fitting collar was fitted such that the two PTFE films are held tightly against the nose of the optical connector as shown in FIG. 1a. Although in this example the attachment was mechanical, other attachment mechanisms are envisioned. Useful examples include the use of pH neutral adhesives or thermal bonding of the membranes to the optical fiber or waveguide. Alternatively, the optical dye can be dissolved or suspended directly in suitable castable polymers such as or polymer solutions which are then applied to an appropriate optical element including fiber optics, planar waveguides, glass slides or reflective surfaces.

Figure 1B:
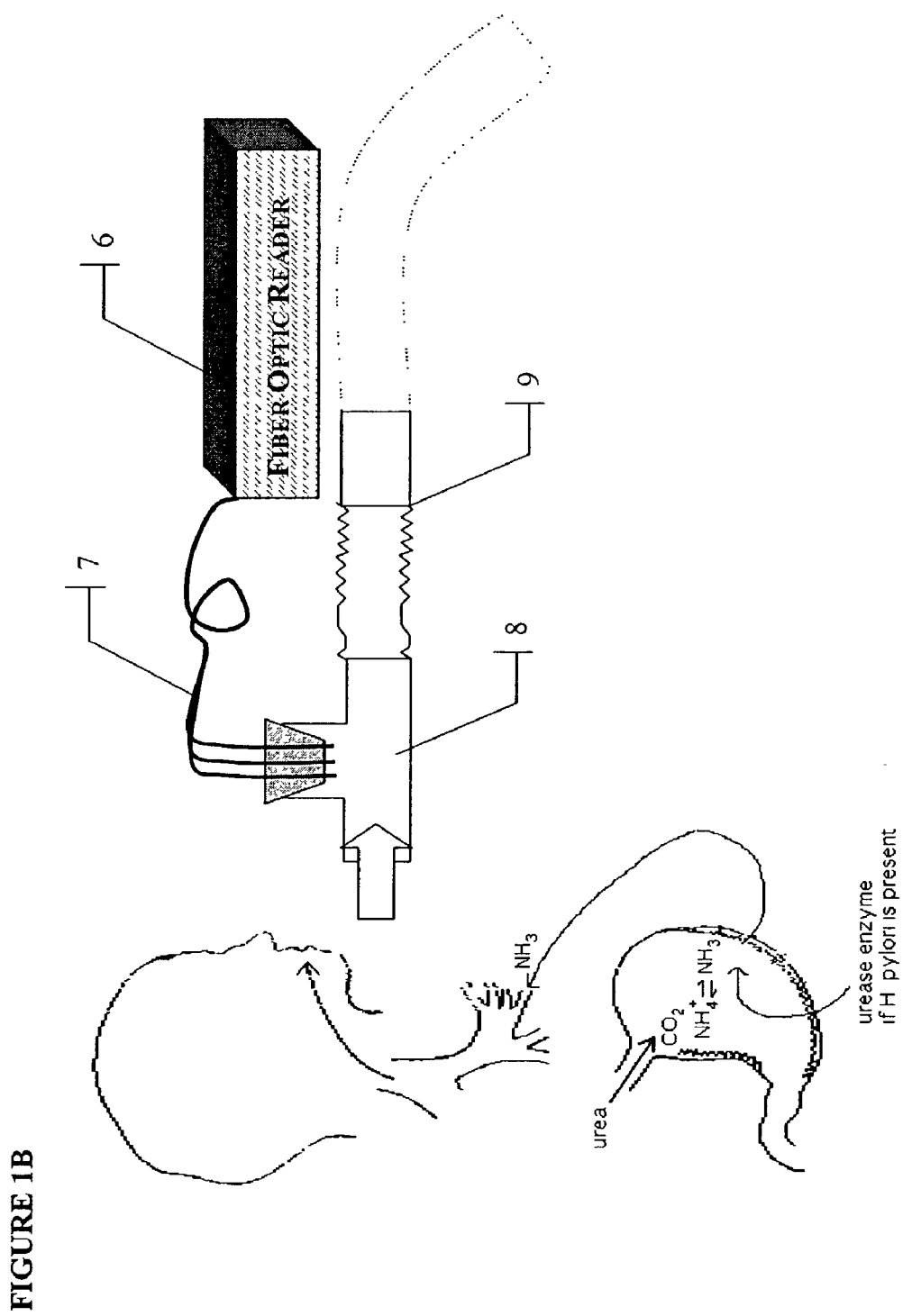
FIG. 1B is a schematic illustrating a fiber optic instrument reader 6, three fiber optic ammonia gas sensors 7 inserted into a gas-impermeable plug, a T-tube 8 with three ports for the subject mouthpiece, the fiber optic sensors in plug and an exhaust port and a breath exhaust tube 9.
Figure 1C:
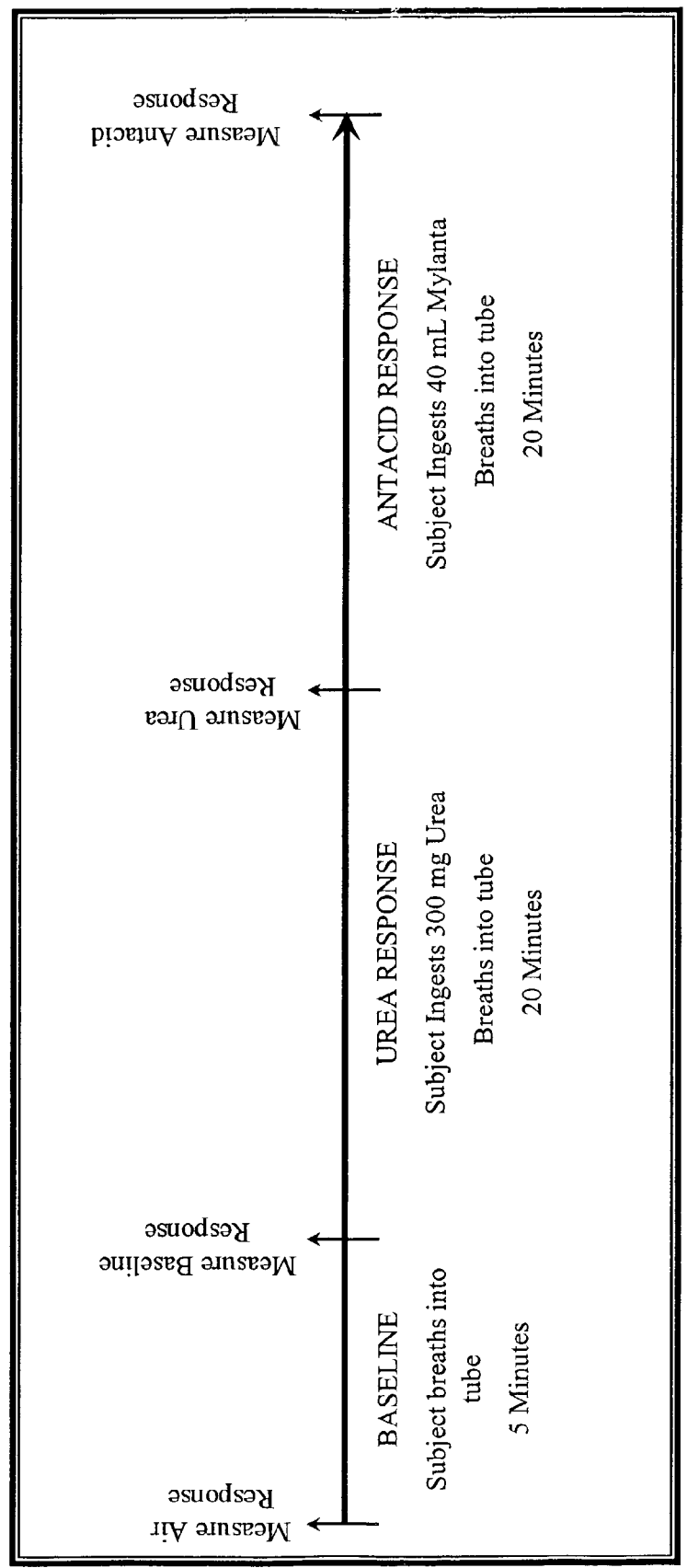
FIG. 1C shows a diagram indicating a representative ABT test sequence.
Figure 2A:
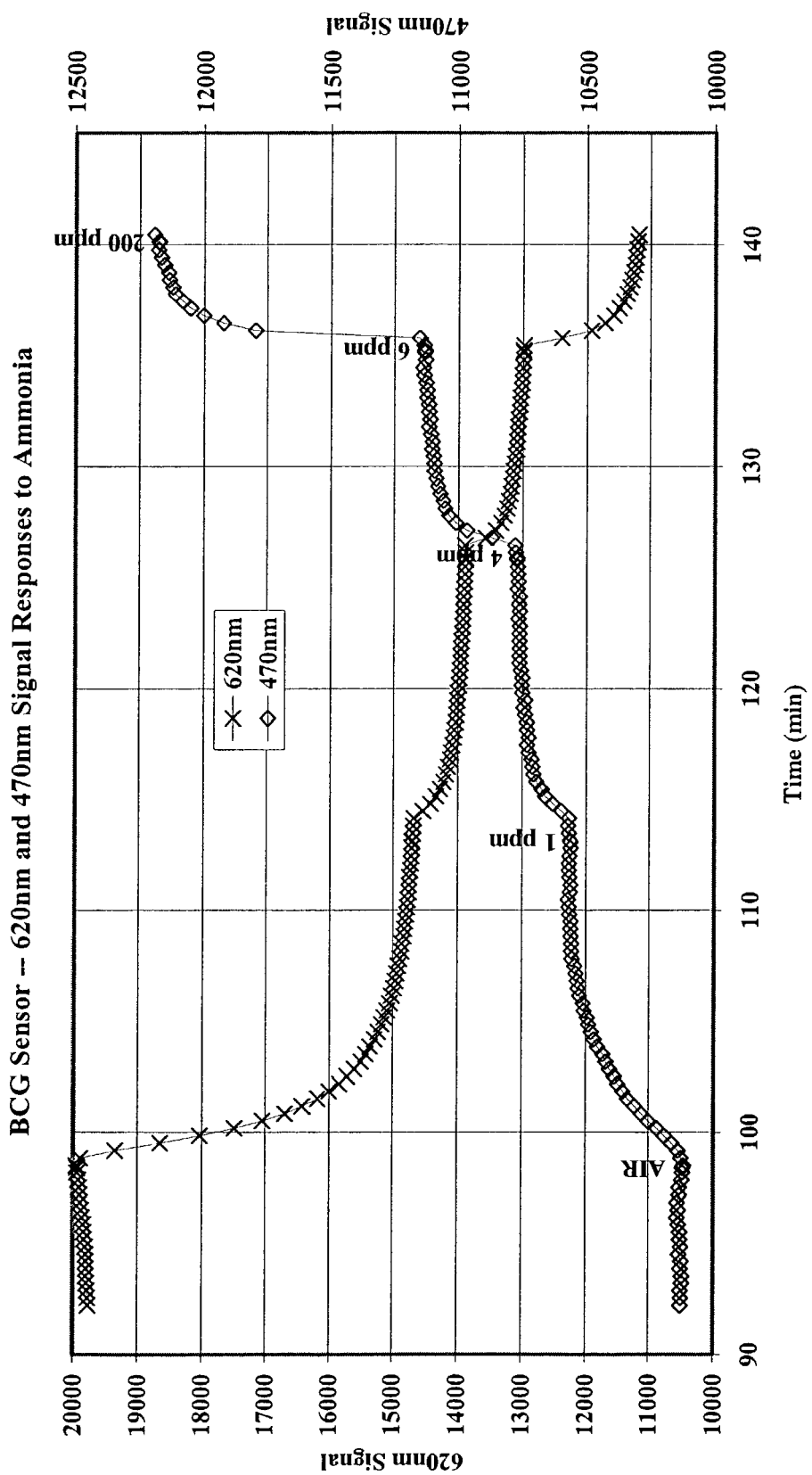
FIG. 2A shows a representative bromocresol green (BCG) sensor reflected signal response change measured at two wavelengths as a function of step changes in ammonia exposure.
Figure 2B:
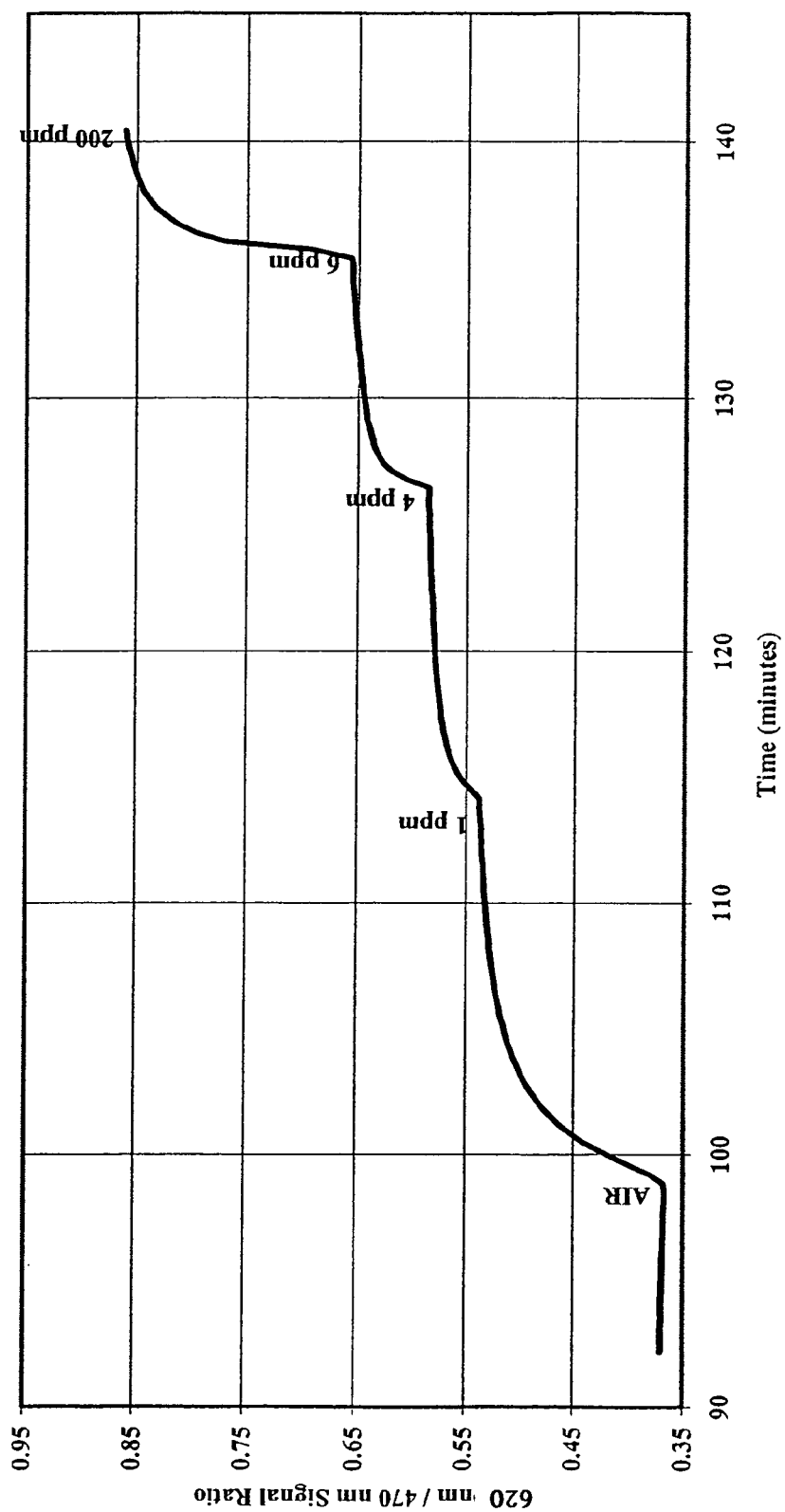
FIG. 2B shows a representative bromocresol green (BCG) sensor calculated signal RATIO response for two wavelengths as a function of step changes in ammonia exposure.
Figure 2C:
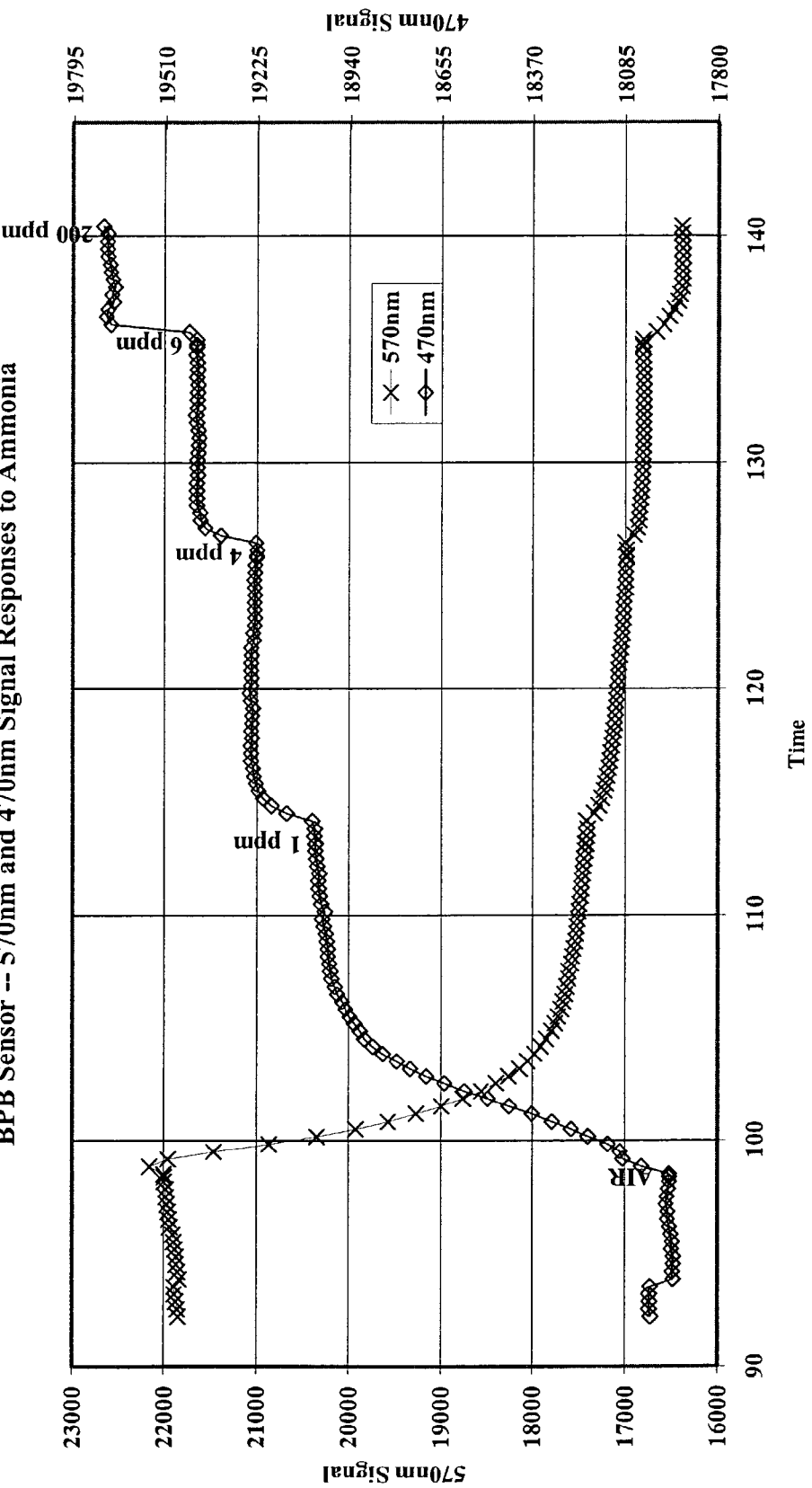
FIG. 2C shows a representative bromophenol blue (BPB) sensor reflected signal response change measured at two wavelengths as a function of step changes in ammonia exposure.
Figure 2D:
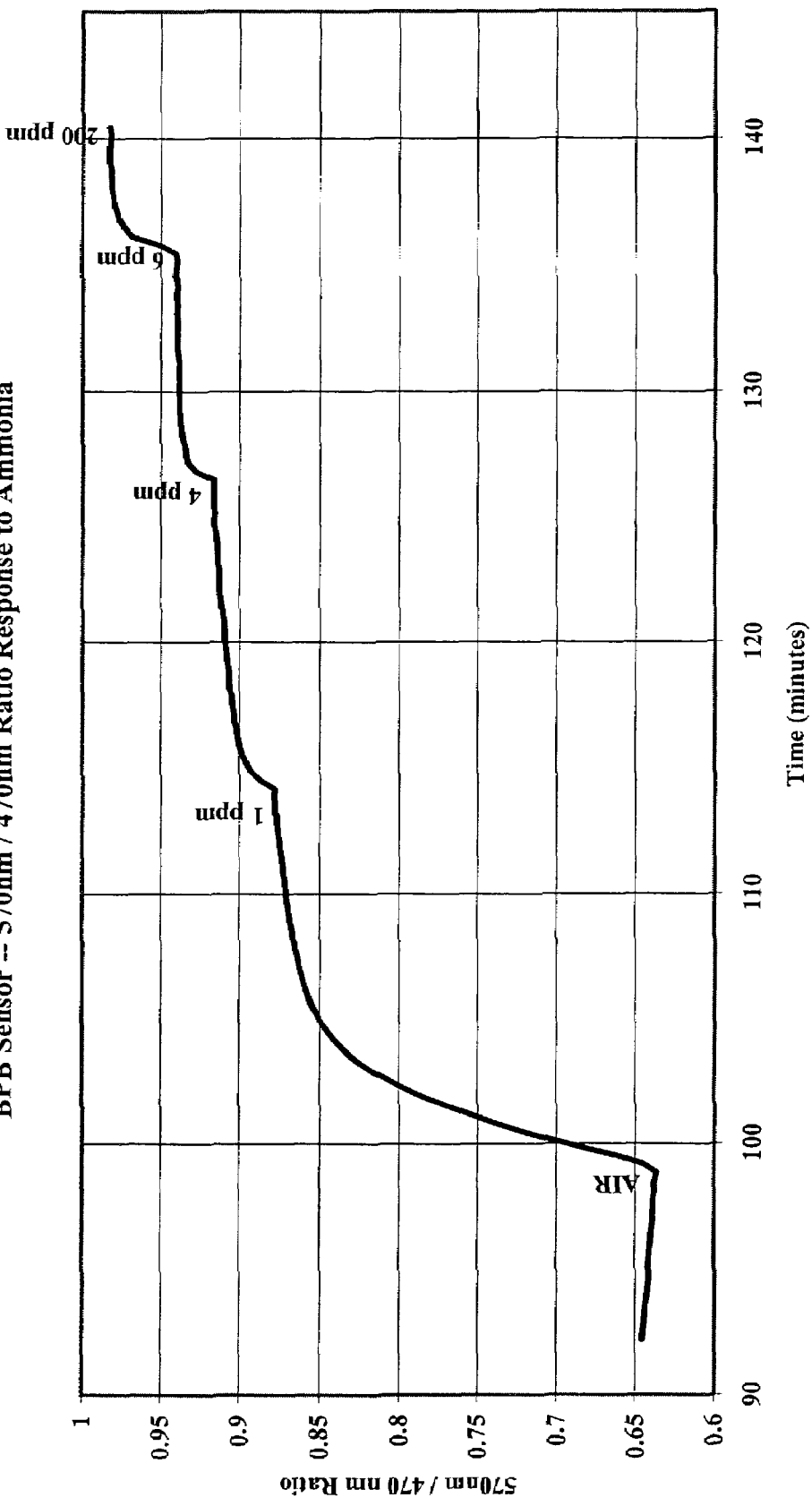
FIG. 2D shows a representative bromophenol blue (BPB) sensor calculated signal RATIO response for two wavelengths as a function of step changes in ammonia exposure.

For *H. pylori* testing of individuals, three sensors (two BPB and one BCG) were inserted into the lumen of a 3-way breathing tube 8, "a T-tube", via the side port. The breath T-tube was also fitted with a disposable mouthpiece. FIG. 1b shows an exemplary breath test sensing device.

The optical sensor films may be placed on a transmissive planar surface and measured by diffuse reflectance spectroscopy or, using suitable optics, by transmission spectroscopy. Similarly, by adhering the ammonia sensitive film to a transmissive planar waveguide, changes in the optical properties of the film may be measured using total internal reflection methods. In another aspect, the ammonia sensitive membrane may be placed on a reflective surface and changes in the film's absorbance spectra measured by conventional reflection spectroscopy methods. Similarly, fluorescent dyes sensitive to ammonia could be used to measure changes in breath ammonia.

It is recognized that other alternate means of measuring ammonia may be available which can measure ammonia on a subject's breath including but not limited to electrochemical sensors, mass spectroscopy, and dye coated silica. To practice the methods described in this invention, the measuring device should provide ammonia sensitivity in the range of 0.05 ppm to 5 ppm. Further, the test measuring device must be able to measure in the presence of water vapor, volatile organics including acetone, with temperature sensitivity coefficients less than 10% of scale.

Instrumentation for Optical Measurement of Ammonia Sensor Responses

The instrument and typical manner of measuring the optical sensor using the instrument is described. Changes in the optical absorbance of the ABT sensor described above were analyzed using solid state optical measurement instruments.

In one embodiment, the measuring instrument is a multifunctional fiber optic sensing system consisting of 3 separate optoelectronic modules, for example, to measure 3 sensors at one time, and control software running on an attached PC. Each module contains two LED's with center wavelength outputs roughly matched to the sensor dye's main absorption band and its isobestic point, hereafter referred to as the Signal Channel and Reference Channels respectively. Modules for measuring BCG sensors utilized LED's with center wavelengths of 620 nm and 470 nm (Hewlett Packard). Modules for measuring BPB sensors utilized 600 nm and 470 nm LED's (Hewlett Packard). Alternatively, the Reference wavelength can be centered in the "Acid Absorption band" (e.g. 430–450 nm for BCG) or a non-absorbing region of the optical dye's spectra (i.e. greater than 700 nm). The LEDs' outputs are coupled into an optical cable with an FC-connector at the distal end to which the ammonia sensor is attached. The instrument alternately activates the LED's transmitting at the two separate wavelengths. The light passes through the sensor tip and returns to the instrument photodetectors after diffusely reflecting off the film. The instrument measures changes in the absorption spectrum of the ammonia sensor as it modulates in the presence of the gas. In addition, the instrument makes continuous reference measurements of the LED intensities and any electronic offsets in each color channel. After normalizing for LED intensity and offsets, the instrument calculates a ratio of the Signal wavelength (i.e. 600 nm or 620 nm) divided by the Reference wavelength intensity (i.e. 470 nm, 430 nm or 700 nm). The wavelength specific signals and Ratio are electronically stored for later analysis.

Example 2

Representative Optical Sensor and Instrument Responses to Ammonia

To establish the sensor responses to ammonia, a BCG and BPB sensor were connected to appropriate modules and then exposed to 0 ppm, 1 ppm, 4 ppm, 6 ppm and 200 ppm of ammonia in water saturated air. The 200 ppm sample saturates the BPB and BCG dye response ranges and was included only to show a full-range response. The individual channel signal levels at the two wavelengths were recorded. Representative optical signal and Ratio plots for these two sensors are shown in FIGS. 2a–d. As predicted from the BPB and BCG pK's, the BPB sensor demonstrates more of its responsivity in the 0–1 ppm range than the BCG sensor that shows a more extended response over the range of 0–6 ppm.

Example 3

Representative *H. pylori* Positive and Negative Subject Ammonia Breath Test Optical Sensor Responses Thirteen volunteers were tested for the presence of *H. pylori* infection using conventional $^{14}$C-urea breath test diagnostic procedures (Ballard Medical, Draper, Utah) in order to classify their clinical status based on current medical practice. Current practice requires subjects fast overnight (typically 8–14 hours) prior to ingesting the $^{14}$C-urea capsule and subsequent collection of the subject's breath. A similar fasting regimen was used for the ammonia breath test (ABT). The breath samples were analyzed for the presence of $^{14}$C using a scintillation counter. A positive urea breath test was defined as breath $^{14}$CO$_2$ excretion greater than 200 dpm, an indeterminate test as breath $^{14}$CO$_2$ excretion of 50–200 dpm, and a negative test as $^{14}$CO$_2$ excretion less than 50 dpm. Five subjects were found positive for *H. pylori* and eight were identified as negative for the organism as measured by this method. One *H. pylori* positive subject (identified as S3 pre-treatment and S14 post-treatment) was tested before and after antibiotic treatment.

To measure the subjects' breath directly with the ABT optical sensor method, the fiber optic ammonia sensors (held at 100% RH/room temperature) were connected up to the fiber optic reader, inserted into the T-tube and monitored for at least about 5 minutes in air. At the end of the air reference measurement, just prior to initiating subject breathing, the data files were annotated with an "AIR" event marker, as a control procedure. Subjects were then asked to breathe normally into the device for about 5 minutes to obtain their basal endogenous breath ammonia measurement, "basal ammonia measure". At the end of the period, the data file was annotated with a "BASELINE" event marker.

Within about 1 minute of the end of the baseline e.g. basal measurement period, each subject was given a 300 mg capsule of unlabeled urea to ingest with 30–40 mL water. This amount of urea was deemed low risk in terms of undesirably affecting study volunteers. Potentially much larger quantities of urea could safely be consumed by individuals for testing purposes. As gelatin capsules were the route of administration utilized for this example, it is recognized that it takes several minutes for the ingested capsule to dissolve in the stomach, release the urea, and achieve dispersion. This factors into the subsequent reported time-course of the subject ammonia-response to urea, "post-urea ammonia measure"; and is therefore reflected in the subsequent definition of the ABT method. It is to be further appreciated that not only the amount but the manner of urea ingestion can be modified which could influence the test time-course. For instance, consumption in liquid form as pre-dissolved urea would be expected to reduce the subject response time. Such modifications are anticipated as optimization of the ABT method.

Following ingestion of the unlabeled urea capsule, in this example immediately after ingestion of the unlabeled urea capsule, subjects resumed breathing into the T-tube sensor device for 16–20 minutes. The end of this data collection time period was annotated with a "UREA" file-event marker. Finally, to assess the affect of a pH modifier, subjects were given 25–30 mL of liquid Mylanta™ antacid to raise the gastric pH and release accumulated ammonium ions in the stomach (total active ingredients of ~2.2 g aluminum hydroxide and 2.2 g magnesium hydroxide). Subjects began breathing into the device for a final 20 minutes and the end of the period, "post-antacid period", was annotated in the data file with an "ANTACID" event marker, indicating the subject's "post-antacid measure".

Figure 3A:
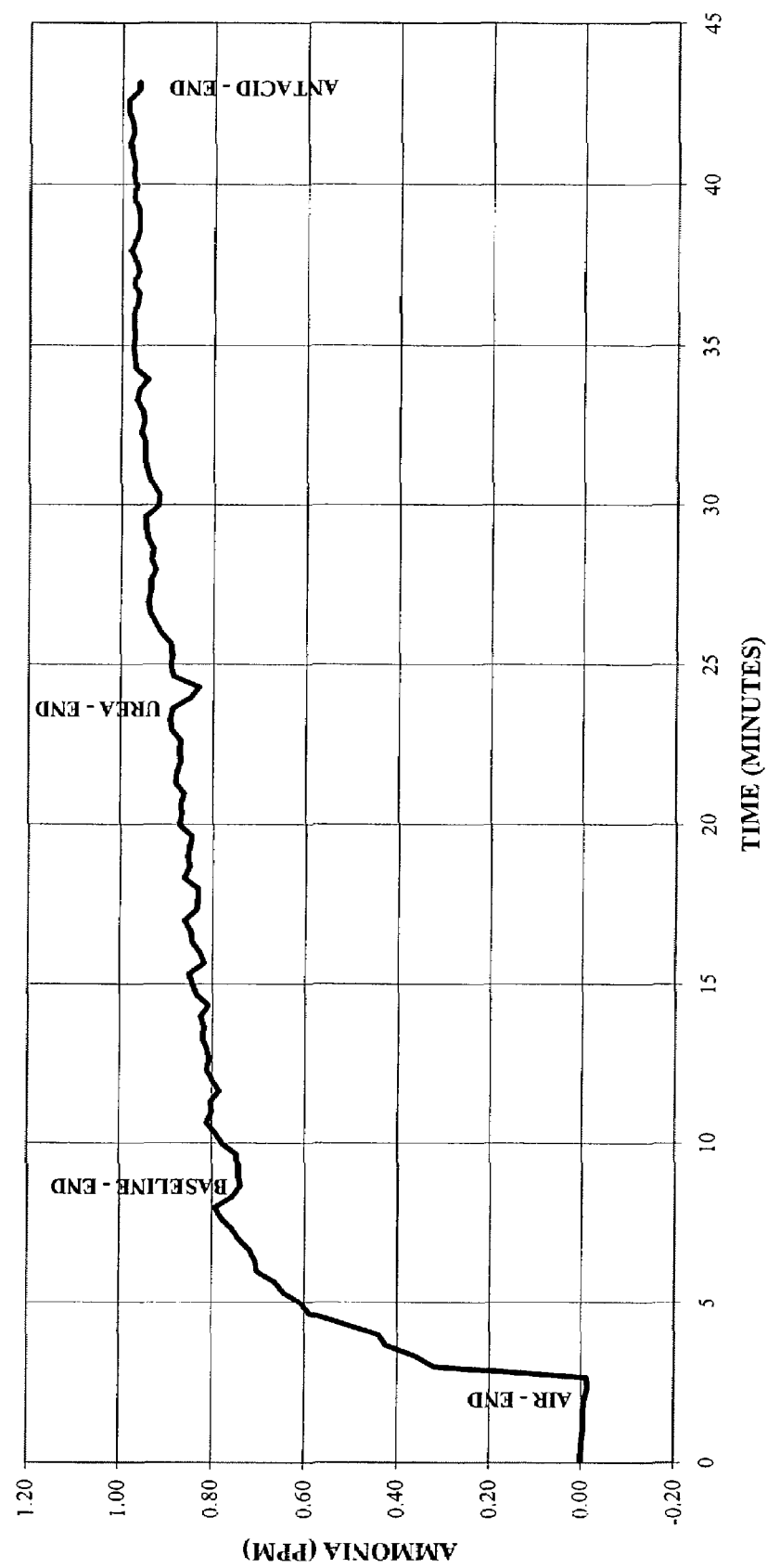
FIG. 3A shows a plot of breath ammonia versus time during an ABT test for an *H. pylori* negative subject.
Figure 3B:
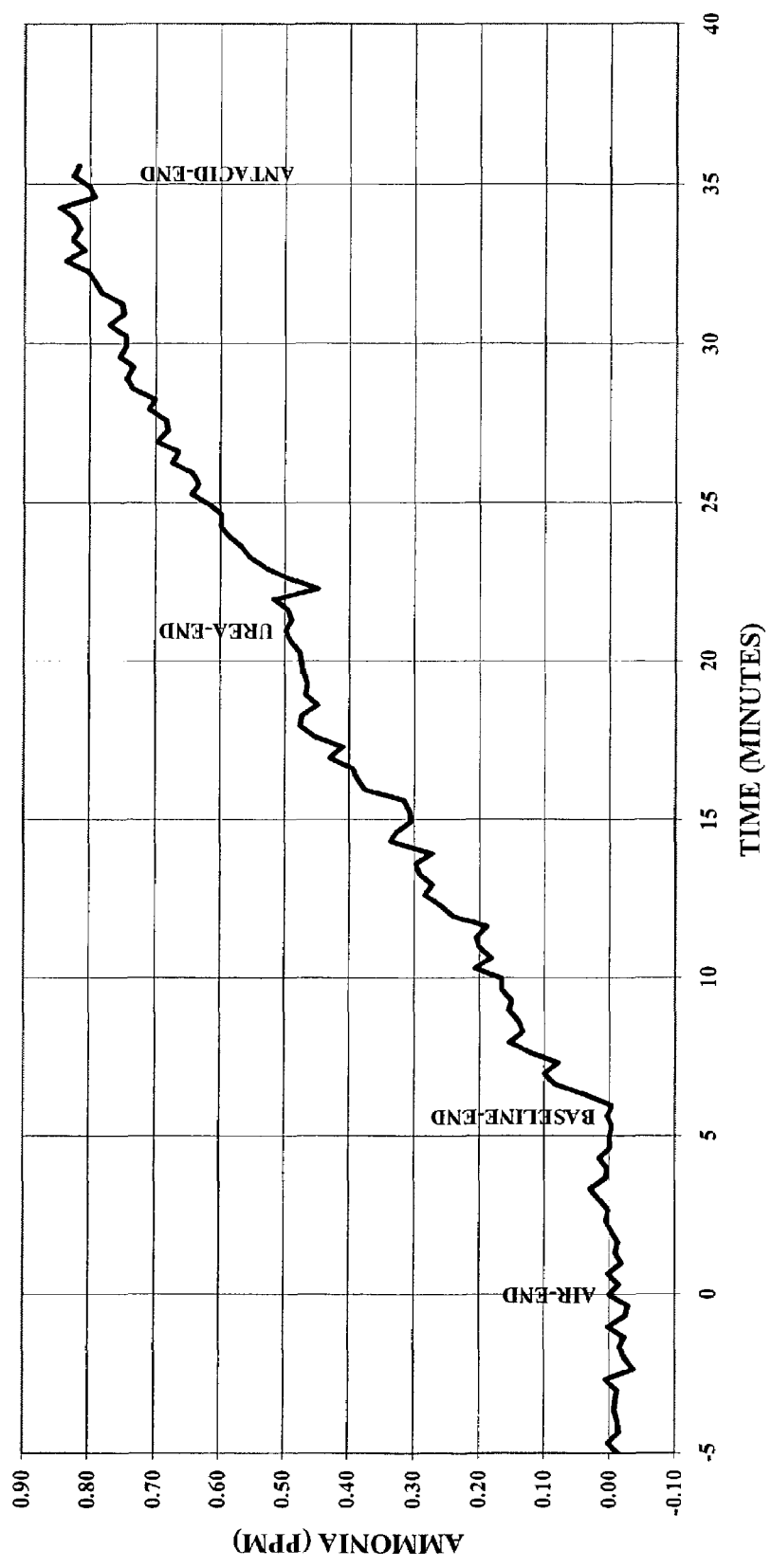
FIG. 3B shows a plot of breath ammonia versus time during an ABT test for an *H. pylori* positive subject.

The signal ratio was a reliable measure of the ammonia sensor response. A representative plot of the sensor ratio for a *H. pylori* negative subject is shown in FIG. 3*a*. A representative plot of the sensor ratio for a *H. pylori* positive subject is shown in FIG. 3*b*. In these figures, the "AIR", "BASELINE", "UREA", and "ANTACID" (for example, Mylanta) test periods are marked by labels that indicate the end of each period.

Comparison of trend plots for *H. pylori* positive and negative subjects showed two distinctive trends. Those subjects negative for *H. pylori* by the $^{14}$C-urea breath test showed: (i) a rapid ammonia signal rise during the baseline period (about 5 minutes following the AIR period) and (ii) minimal change in the sensor response after ingestion of the urea capsule. In contrast, subjects positive for *H. pylori* showed: (i) a remarkably flat baseline period response, followed by (ii) a marked rise in the ammonia signal after administration of the urea capsule. Note the lack of a sharp increase in the baseline response. The marked response to the urea capsule is especially prominent in comparison to the low baseline response of these *H. pylori* infected subjects.

Example 4

Ammonia Breath Measures for *H. pylori* Positive and Negative Subjects

The following example teaches the use of the baseline (basal) ammonia measure to determine an individual's *H. pylori* status.

The signal Ratio data collected for the thirteen volunteers was converted to an absolute ammonia measure using a post-test calibration. Calibrants were prepared from pH adjusted phosphate buffered ammonium chloride solutions. By using the equilibrium ammonia gas concentration predicted from Henderson-Hasselbach, water saturated calibrant ammonia gasses were prepared. The predicted headspace ammonia gas was corroborated using an Orion ion selective electrode.

Sensors were exposed to several headspace gas buffers and allowed to equilibrate for 20 minutes. Using the final Ratio value attained in these calibration solutions, calibration coefficients were calculated for each sensor. The continuous Ratio values for each sensor recorded during the breath test were then converted to ammonia concentrations (ppm) using these calibration coefficients. Finally, the average absolute ammonia measure indicated by the three sensors was computed for tabulation and correlation to *H. pylori* status.

Although this example demonstrates the use of calibrants to calculate the ammonia concentration of a subject's breath, any method that allows nomalization of sensor responses to a standard are equally useful and diagnostic.

The average of the two BPB and one BCG sensors' calculated ammonia for each subject (no excluded sensors or data points) is shown in Table 1.

TABLE 1

Calculated ammonia values for test subjects 1–14

| Subject | Status | dpm† | Air | Baseline | Urea | Antacid |
|---|---|---|---|---|---|---|
| S1 | Neg | 9 | 0.000 | 0.966 | 0.822 | 1.002 |
| S2 | Neg | 42 | 0.000 | 0.752 | 0.796 | 0.861 |
| S3 | Pos | 817 | 0.000 | −0.078 | 0.595 | 0.878 |
| S4 | Pos | 2030 | 0.000 | 0.050 | 0.795 | 1.098 |
| S5 | Pos | 1969 | 0.000 | 0.174 | 0.520 | 0.595 |

TABLE 1-continued

Calculated ammonia values for test subjects 1–14

| Subject | Status | dpm[†] | Air | Baseline | Urea | Antacid |
|---|---|---|---|---|---|---|
| S6 | Neg | 27 | 0.000 | 0.465 | 0.550 | 0.659 |
| S7 | Neg | 10 | 0.000 | 0.262 | 0.402 | 0.410 |
| S8 | Pos | 922 | 0.000 | 0.022 | 0.076 | 0.128 |
| S9 | Neg | 0 | 0.000 | 0.361 | 0.557 | 0.625 |
| S10 | neg | 22 | 0.000 | 0.411 | 0.815 | 0.866 |
| S11 | Neg | 4 | 0.000 | 0.223 | 0.360 | 0.285 |
| S12 | Neg | 0 | 0.000 | 0.545 | 0.749 | 0.734 |
| S13 | Pos | 1375 | 0.000 | 0.022 | 0.232 | 0.704 |
| S14* | Neg | 3 | 0.000 | 0.417 | 0.504 | 0.935 |

[†]dpm > 200 defined as *H. pylori* positive.
*S14 is a retest of S3 6-weeks after treatment for *H. pylori* infection There was a wide range of breath ammonia values in the baseline period for *H. pylori* negative subjects, ranging from about 0.97 ppm to about 0.22 ppm. Remarkably, and surprising, all *H. pylori* positive subjects had lower average basal ammonia levels than *H. pylori* negative subjects did. The average absolute basal ammonia measure was significantly lower among *H. pylori* positive subjects as compared to *H. pylori* negative subjects (0.04 ppm vs. 0.49 ppm, p=0.002). In contrast, there was no significant difference between the two groups in their post-urea ammonia measures (0.44 ppm vs. 0.62 ppm respectively, p=0.19) or post-antacid ammonia measures (0.68 ppm vs. 0.71 ppm respectively, p=0.86).

Figure 4:
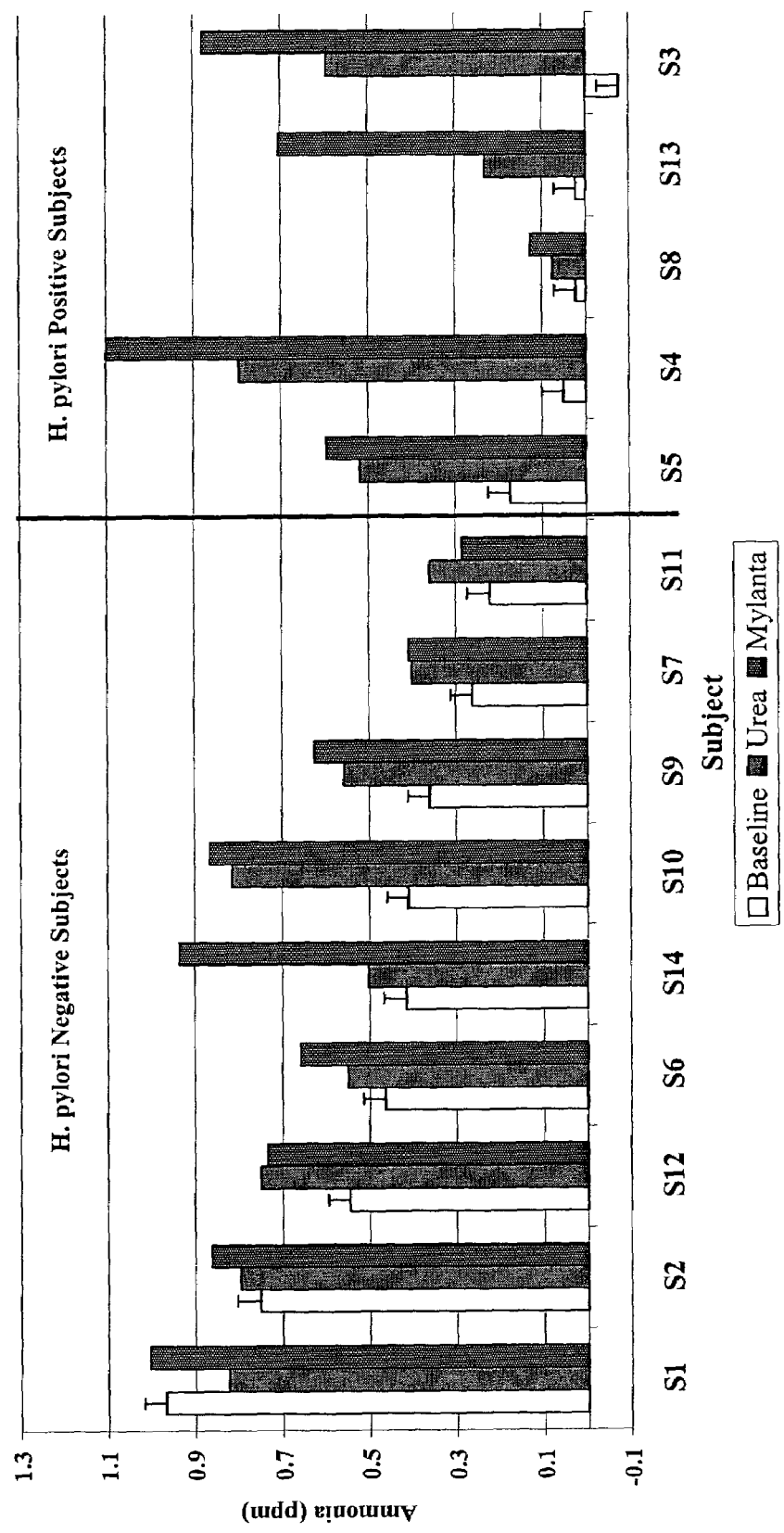
FIG. 4 shows a bar chart indicating differentiation of *H. pylori* negative and positive individuals based on higher BASELINE (Basal) ammonia breath measures (white bars) in negative individuals than observed in *H. pylori* positive individuals. The chart also shows lack of difference in absolute breath ammonia measure after administration of UREA.

FIG. 4 shows the breath ammonia data from the preceding table in a manner showing the basis for differentiating infection status based on the measured basal ammonia. The graph shows that a large group of uninfected individuals can be differentiated from infected individuals based on the former's higher basal ammonia measures. Several individuals (S7, S11, and S5) had intermediate basal breath ammonia measures and would require further analysis of their urea or antacid test result to differentiate their status. It is also significant to note that 2 weeks after completing antibiotic treatment, subject S3 (retested as S14) demonstrated a reversion in their basal ammonia breath test value from essentially no ammonia to over 0.4 ppm, well above the intermediate level.

Surprisingly, the breath ammonia measure alone after administering urea was not diagnostic of *H. pylori* infection status. It can be anticipated that increasing the dosage of urea may have increased the ammonia breath level of this group sufficiently to differentiate positive and negative individuals. Similarly, increasing the measurement time to allow for greater urease hydrolysis of the urea might also be used to increase the ammonia breath levels.

Percent Change Urea/Baseline

The ammonia measures for *H. pylori* positive and negative subjects were not significantly different after administering the urea capsule. The relative change in ammonia measure between the basal ammonia measure and post-urea ammonia measure and between the baseline and post-antacid ammonia measures were analyzed. The percentage change between the basal and post-urea ammonia measures was calculated simply as:

$$\%(B-U)\text{change} = \{(Ammonia_{urea} - Ammonia_{baseline})/Ammonia_{baseline}\} \times 100$$

A similar calculation of the percent change from basal to post-antacid and from post-urea to post-antacid (i.e. % B–M and % U–M respectively) was made. The results of these calculations are shown in Table 2. The data has been sorted on the subject's $^{14}$C-urea breath test status and their basal ammonia measure.

TABLE 2

| Subject | [14]C UBT Status | dpm | Baseline | Post Urea | Post antacid | % change: urea vs baseline[a] | % change: antacid vs baseline[b] | % change: antacid vs urea[c] |
|---|---|---|---|---|---|---|---|---|
| S1 | Neg | 9 | 0.97 | 0.82 | 1.00 | 15% | 4% | 22% |
| S2 | Neg | 42 | 0.75 | 0.80 | 0.86 | 6% | 15% | 8% |
| S12 | Neg | 0 | 0.55 | 0.75 | 0.73 | 37% | 35% | 2% |
| S6 | Neg | 27 | 0.47 | 0.55 | 0.66 | 18% | 42% | 20% |
| S14 | Neg | 3 | 0.42 | 0.50 | 0.94 | 21% | 124% | 86% |
| S10 | Neg | 13 | 0.41 | 0.81 | 0.87 | 98% | 111% | 6% |
| S9 | Neg | 0 | 0.36 | 0.56 | 0.62 | 55% | 73% | 12% |
| S7 | Neg | 10 | 0.26 | 0.40 | 0.41 | 53% | 56% | 2% |
| S11 | Neg | 4 | 0.22 | 0.36 | 0.28 | 62% | 28% | 21% |
| S5 | Pos | 1969 | 0.17 | 0.52 | 0.59 | 198% | 241% | 14% |
| S4 | Pos | 2030 | 0.05 | 0.80 | 1.10 | 1494% | 2101% | 38% |
| S8 | Pos | 922 | 0.02 | 0.08 | 0.13 | 241% | 473% | 68% |
| S13 | Pos | 1375 | 0.02 | 0.23 | 0.70 | 945% | 3073% | 204% |
| S3 | Pos | 817 | −0.08 | 0.60 | 0.88 | 866% | 1230% | 48% |

Figure 5:
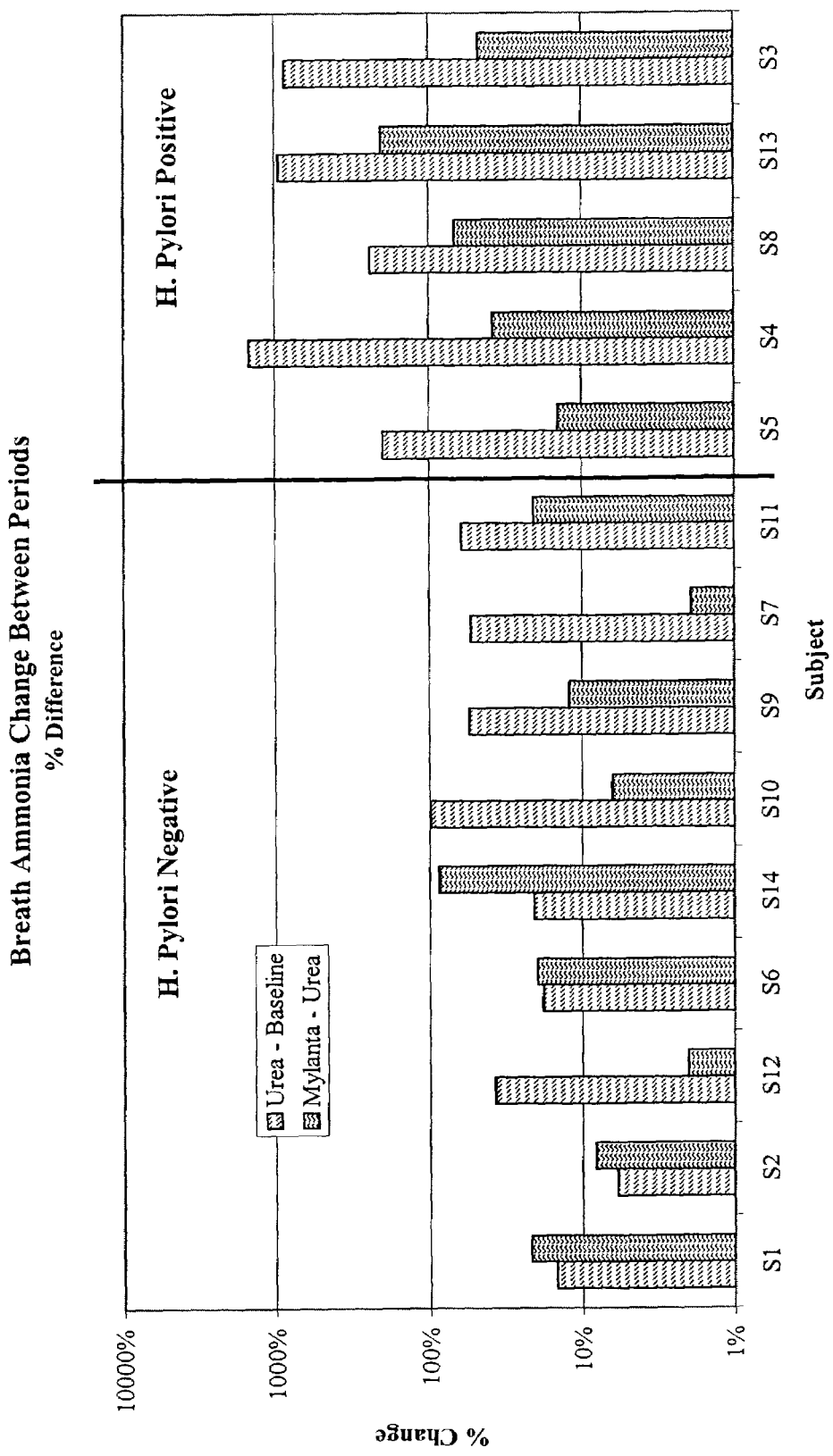
FIG. 5 shows a bar chart (log scale) indicating differentiation of *H. pylori* negative and positive individuals based on a larger percentage increase in breath ammonia measures after urea administration for positive individuals than that observed in negative individuals.

Table 2 indicates that the *H. pylori* positive subjects demonstrate a much higher percentage increase between their basal and post-urea ammonia measures than the *H. pylori* negative subjects. Similarly, the percentage increase between the basal and post-antacid ammonia measures was significantly higher for the infected versus uninfected individuals. These differences are also shown in FIG. 5.

The percentage change is particularly useful in differentiating between subjects with intermediate baseline responses such as those exhibited by S7, S11 and S5. The high percentage change in ammonia measure after urea ingestion allowed the *H. pylori* positive subject 5 to be clearly differentiated from the *H. pylori* negative subjects 7 and 11.

Example 5

Use of pH Modifier to Enhance Breath Ammonia

An antacid was used to modify the gastric pH and the effect on breath ammonia measures.

Ammonia produced by the *H. pylori* organisms is expected to be immediately converted to $NH_4^+$ ammonium ions due to the low pH of gastric juice. Ions do not readily cross the stomach lining and as such, ammonium would be expected to accumulate in the stomach with only the small portion of ammonia ($NH_3$) in equilibrium passing through the stomach lining and into the blood. Raising the gastric juice contents would be expected to increase the concentration of $NH_3$ in equilibrium with $NH_4^+$ ions and so raise the blood concentration of ammonia.

The stomach pH was increased by drinking 40 mL of an antacid (80 mg aluminum hydroxide plus 80 mg magnesium hydroxide per mL) about 20 minutes after a subject had ingested 300 mg of urea. Presumably, this should raise the gastric juice pH by 2–5 pH units, thereby increasing the ammonia concentration by 100 to 10,000 fold as predicted by the Henderson-Hasselbach relationship of pH and concentration for weak acids and bases. The average percentage increase in breath ammonia for the *H. pylori* positive subjects was 74% versus an increase of 20% for the negative subjects. Although the averages were not statistically different (p=0.08) from each other, there is a strong indication that inclusion of an antacid could be used to further differentiate the two populations. Either insufficient antacid was administered to effect the desired change or an antacid with a higher pH might have released the ammonia in a manner adequate to achieve a statistically different measure.

Example 6

Determination of Status from Baseline Ammonia Breath Test & Urea Confirmation

In the following, a method for differentiating indeterminate baseline breath ammonia values for *H. pylori* positive and negative subjects.

Example 4 shows that 10 of 13 subject's *H. pylori* status can be readily determined from their Baseline ammonia breath test value alone. Namely, *H. pylori* negative subjects demonstrated significantly higher baseline ammonia measures than *H. pylori* positive subjects.

From the table in Example 4, *H. pylori* negative subjects S7 and S11 demonstrate Baseline breath ammonia measures of 0.26 ppm and 0.22 ppm respectively. These values are similar to those for the *H. pylori* positive subject S5 (0.17 ppm). However, as identified in Example 4, *H. pylori* positive subjects demonstrated a larger percentage increase in their post-urea ammonia breath measures than the *H. pylori* negative subjects, making it possible to discriminate between those subjects with breath ammonia values judged to be indeterminate by absolute normative standards.

No license is expressly or implicitly granted to any patent or patent applications referred to or incorporated herein. The discussion above is descriptive, illustrative and exemplary and is not to be taken as limiting the scope defined by any appended claims.

We claim:

1. A method for detecting the presence or absence of *H. pylori* infection in an individual comprising:
    a) exposing at least one ammonia sensitive sensor to expiration of an individual, wherein where more than one sensor is exposed, the sensors are exposed to identical samples of respiration;
    b) deriving, based on response of the at least one sensor to the exposure, a basal ammonia measure of expired ammonia over a basal measurement period; and
    c) comparing the basal ammonia measure against a normative value that reflects at least one of a *H. pylori* positive population measure and a *H. pylori* negative population measure, wherein the *H. pylori* status of the individual is determined.

2. The method of claim 1, further comprising:
    a) administering a *H. pylori* urease enzyme substrate following determination of the basal ammonia measure;
    b) deriving a post-substrate ammonia measure of expired ammonia over a post-urea measurement period of about 10 minutes to about 90 minutes after the administration of the substrate; and
    c) comparing at least one measure of expired ammonia selected from the group consisting of the absolute measure of the post-substrate period, the absolute difference between the measures of the basal period and post-substrate period, the relative change between the measures of the basal period and post-substrate period, and, the rate of change in expired ammonia measures during the post-substrate period, against a normative value that reflects at least one of a *H. pylori* positive and a *H. pylori* negative population measures, wherein the *H. pylori* status of the individual is determined.

3. The method of claim 2, further comprising:
    a) administering an agent intended to increase expired ammonia either coincident or subsequent to administration of the *H. pylori* urease enzyme substrate;
    b) deriving a post-substrate and post-agent ammonia measure of expired ammonia over a post-agent measurement period of about 10 minutes to about 90 minutes after ingestion of the substrate and agent; and
    c) comparing at least one measure of expired ammonia selected from the group consisting of the absolute measure of the post-agent period, the absolute difference between the measure of the basal period, post-urea period and post-agent period, the relative change between the measures of the basal period, post-urea period, and post-agent period, and, the rate of change in expired ammonia measures during the basal period, post-substrate period, and post-agent period, against a normative value that reflects at least one of a *H. pylori* positive and *H. pylori* negative population values, wherein the *H. pylori* status of the individual is determined.

4. The method of claim 3, wherein the agent intended to increase expired ammonia either coincident or subsequent to administration of the *H. pylori urease enzyme substrate is an antacid*.

5. The method of claim 3, wherein the agent intended to increase expired ammonia either coincident or subsequent to administration of the *H. pylori* urease enzyme substrate comprises about 2 g aluminum hydroxide and about 2 g magnesium hydroxide.

6. The method of claim 1, 2 or 3, wherein the individual undergoing testing fasts for at least 8 hours before initiation of the method.

7. The method of claim 1, wherein the at least one ammonia sensitive sensor has a sensitivity to ammonia in the range of about 0.05 ppm to about 5 ppm.

8. The method of claim 1, wherein the ammonia sensitive sensor is an optical sensor for expired ammonia, comprising:
    a solid substrate; and
    an ammonia sensitive indicator dye having measurable spectral characteristics immobilized in or on the solid substrate so that exposure of the dye to expired ammonia causes a change in the spectral characteristics of the ammonia-sensitive indicator dye.

9. The method of claim 8, wherein the substrate is polytetrafluorethylene.

10. The method of claim 8, wherein the indicator dye is a non-water soluble pH indicator dye.

11. The method of claim 8, wherein the substrate is an ammonia permeable solid-phase film.

12. The method of claim 10, wherein the indicator dye is a weak acid compound that undergoes changes in its absorption spectra upon acid/base dissociation.

13. The method of claim 12 wherein the weak acid compound is selected from the group consisting of bromocresol green and bromophenol purple.

14. The method of claim 8, wherein the substrate is a gas permeable hydrophobic polymer.

15. The method of claim 14, wherein the hydrophobic polymer is a substituted ethylenic polymer.

16. The method of claim 8, wherein the substrate is porous.

17. The method of claim 1, wherein comparing the basal ammonia measure in c) comprises comparing a basal ammonia measure selected from the group consisting of: an absolute value measurement; a rate of change measurement; and combinations thereof.

18. The method of claim 1, wherein where more than one sensor is exposed, the sensors are exposed to the identical respiration samples within a single chamber.

19. The method of claim 1, wherein where more than one sensor is exposed, the sensors are exposed to identical respiration samples in different chambers.

* * * * *